United States Patent [19]

Hull, Jr.

[11] Patent Number: 4,999,427

[45] Date of Patent: Mar. 12, 1991

[54] PROCESS FOR THE PREPARATION OF 2-ALKYLPYRIMIDINES

[75] Inventor: John Hull, Jr., Midland, Mich.

[73] Assignee: DowElanco, Indianapolis, Ind.

[21] Appl. No.: 195,043

[22] Filed: May 16, 1988

[51] Int. Cl.$^5$ .......................................... C07D 239/26
[52] U.S. Cl. ...................................... 544/242; 564/159
[58] Field of Search .......................................... 544/242

[56] References Cited

U.S. PATENT DOCUMENTS

| | | | |
|---|---|---|---|
| 3,050,523 | 8/1962 | Erner et al. | 544/242 |
| 3,126,381 | 3/1964 | Langis et al. | 544/242 |
| 3,366,634 | 1/1968 | McBride, Jr. et al. | 544/242 |
| 3,483,203 | 12/1969 | Werner | 544/242 |
| 4,376,201 | 3/1983 | Pews | 544/242 |
| 4,493,929 | 1/1985 | Pews | 544/242 |
| 4,719,299 | 1/1988 | Van der Stoel | 544/242 |
| 4,775,755 | 10/1988 | Teunissen | 544/242 |
| 4,880,929 | 11/1989 | Teunissen et al. | 544/242 |

FOREIGN PATENT DOCUMENTS

| | | |
|---|---|---|
| 0117882 | 9/1984 | European Pat. Off. . |
| 0192297 | 8/1986 | European Pat. Off. . |
| 0192299 | 8/1986 | European Pat. Off. . |
| 0193973 | 9/1986 | European Pat. Off. ............ 544/242 |
| 8603168 | 7/1988 | Netherlands ........................ 544/242 |

OTHER PUBLICATIONS

Aspinall, J. Am. Chem. Soc., vol. 62, pp. 2160–2162 (08/40).
Tsuchiya, et al., Yakugaku Zasshi, vol. 96(8), pp. 1005–1012 (1976), English translation supplied.
Tsuchiya, et al., Yakugaku Zasshi, vol. 97(4), pp. 373–381 (1977), English translation supplied.

Primary Examiner—Diana Rivers
Attorney, Agent, or Firm—Craig E. Mixan; Ronald G. Brookens

[57] ABSTRACT

2-Alkylpyrimidines are prepared from 1,3-diaminopropane and an appropriate alkanecarboxylic acid in a continuous vapor phase process without isolating any of the reaction intermediates. Improvements in each reaction step, namely, the amidation, the cyclization/dehydration and the dehydrogenation, contribute to the overall success of the continuous vapor phase process.

4 Claims, 1 Drawing Sheet

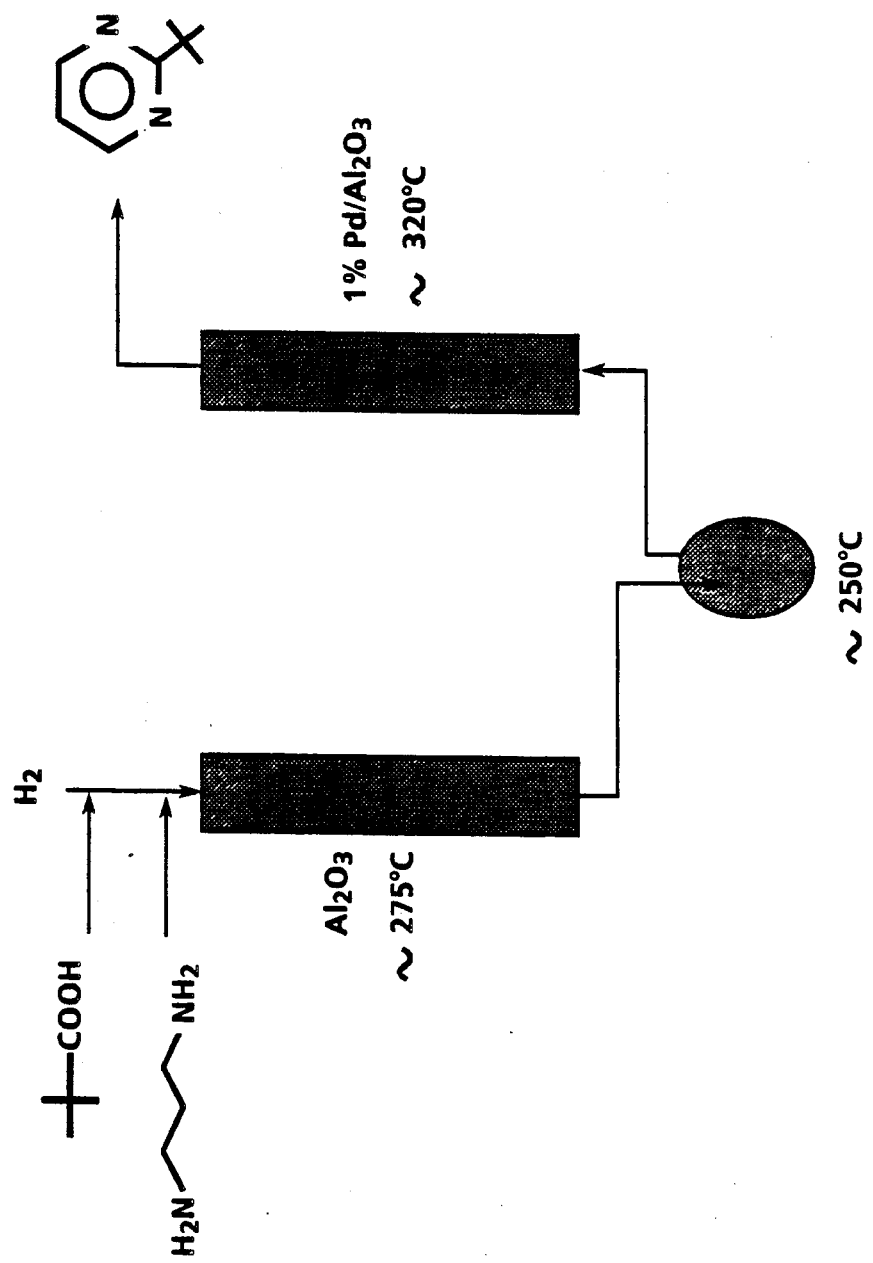

PROCESS FOR THE PREPARATION OF 2-ALKYLPYRIMIDINES

FIELD OF INVENTION

The present invention relates to an improved process for the preparation of 2-alkylpyrimidines. More specifically, the present invention relates to improvements in the multistep conversion of 1,3-diaminopropane and an alkanecarboxylic acid to a 2-alkylpyrimidine.

BACKGROUND OF THE INVENTION

2-Alkylpyrimidines, particularly 2-tert-butylpyrimidine, are advantageously employed as intermediates for the preparation of insecticidal O- -alkyl-O-pyrimidin-(5)-yl]-(thiono)(thiol)-phosphoric (phosphonic) acid esters or ester amides as described in U.S. Pat. No. 4,127,652.

The preparation of 2-alkylpyrimidines is taught in U.S. Pat. No. 3,050,523. That process requires the reaction of an alkylene 1,3-diamine with an organic carboxylic acid, ester or amide over a supported noble metal catalyst having dehydration and dehydrogenation activity. The desired compounds may be isolated by azeotropic distillation or by treatment with carbon dioxide followed by distillation. The work-up procedures are time consuming and the yields are not as good as could be desired.

More recently, the individual steps (a-c) of the conversion of 1,3-diaminopropane and an alkanecarboxylic acid to a 2-alkylpyrimidine have been investigated; see, for example, U.S. Pat. Nos. 4,376,201 and 4,493,929 and European Patent Application Publication Nos. 117,882, 192,297 and 192,299.

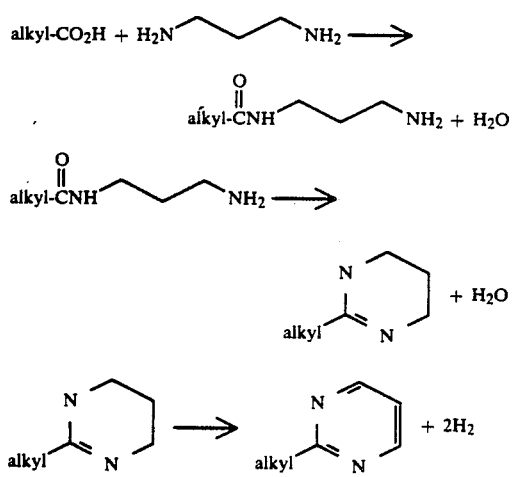

U.S. Pat. No. 4,376,201 describes the vapor phase reaction wherein a 3-aminopropyl carboxylic acid amide is cyclized and dehydrogenated over a supported platinum or palladium catalyst (steps b+c).

U.S. Pat. No. 4,493,929 describes the separation of steps b+c and the improved vapor phase reaction wherein 2-alkylpyrimidines are obtained in high yield and purity by the dehydrogenation of a 2-alkyltetrahydropyrimidine under conditions which do not generate water and in which no water is added (step c).

European Patent Application Publication No. 117,882 describes an overall process for the preparation of 2-tert-butylpyrimidine which comprises the following individual steps: a) the preparation of 3-aminopropyl pivalamide by reaction of pivalic acid and an excess of 1,3-diaminopropane: b) removal of unreacted 1,3-diaminopropane by distillation and dehydration of the 3-aminopropyl pivalamide to 2-tert-butyl-1,4,5,6-tetrahydropyrimidine in the liquid phase, preferably in the presence of a solvent capable of azeotroping water: and c) the dehydrogenation of 2-tert -butyltetrahydropyrimidine to 2-tert- -butylpyrimidine, under conditions in which water is neither generated nor added, over a supported noble metal catalyst.

European Patent Application Publication No. 192,297 describes the vapor phase dehydrogenation of 2-propyl- or 2-butyl-1,4,5,6-tetrahydropyrimidine over a palladium containing catalyst in which the catalyst lifetime is prolonged by operating the presence of carbon monoxide and hydrogen (step c).

European Patent Application Publication No. 192,299 describes the multistep preparation of 2-methyl- and 2-ethylpyrimidine by: the reaction of an acetic or propionic acid derivative with 1,3-diaminopropane in the liquid phase to form a 1-amino-3-amidopropane (step a): optional cyclization to the 2-methyl- and 2-ethyltetrahydropyrimidine (step.b): and gas phase dehydrogenation and optional cyclization to 2-methyl- and 2-ethylpyrimidine with a palladium-containing catalyst in the presence of carbon monoxide and hydrogen (step c or steps b+c).

Thus, although the direct conversion of 1,3-diaminopropane and an alkanecarboxylic acid to a 2-alkylpyrimidine was originally conceived in U.S. Pat. No. 3,050,523, the cumbersome work-up procedures and poor yields of that original disclosure prompted subsequent researchers to recommend improved stepwise approaches to the desired conversion.

SUMMARY OF THE INVENTION

The present invention relates to an improved continuous process for the preparation of 2-alkylpyrimidines from 1,3-diaminopropane and an alkanecarboxylic acid without the isolation of any reaction intermediates. Furthermore, the present invention relates to a series of individual improvements in the reaction steps a-c which contribute to the continuous production of 2-alkylpyrimidines.

Previously, the art described the cyclization of a 3-aminopropyl alkanecarboxylic acid amide to the corresponding 2-alkyltetrahydropyrimidine (step b) and the sequential dehydrogenation of the 2- -alkyltetrahydropyrimidine to a 2-alkylpyrimidine (step c) in a single vapor phase reaction over a supported noble metal catalyst. The poor yields associated with this process have fostered a more recent recommendation to separate steps b and c and to perform the cyclization (step b) in the liquid phase. The cyclization of a 3-aminopropyl alkanecarboxylic acid amide to a 2-alkyltetrahydropyrimidine is normally conducted by reflux in a high boiling organic solvent with concurrent removal of water. 2-Tert-butyl-tetrahydropyrimidine thus obtained can either be isolated by crystallization, or dehydrogenated directly without isolation. However, the crystallization requires additional and cumbersome unit operations, and many of the solvents used in the ring-closure reaction are not suitable for the dehydrogenation reaction. One aspect of the present invention is an improved process for the preparation of a 2-alkyl-1,4,5,6- -tetrahydropyrimidine from a 3-aminopropyl alkanecarboxylic acid amide which comprises passing the 3-aminopropyl alkanecarboxylic acid amide in the vapor phase over an acidic catalyst. This improvement provides increased yields and eliminates the need for cumbersome unit operations such as the isolation of a solid by crystallization from an organic solvent.

2-Tert-butyl-tetrahydropyrimidine is a sublimable solid with a propensity to plug feed lines and condensors in batch operations. The direct use of the tetrahydropyrimidine as produced above without isolation would combat these difficulties, but the cyclization reaction (step b) also produces an equivalent of water. The prior art teaches the deleterious effect of water on the dehydrogenation reaction. Another aspect of the present invention is an improved process for the preparation of a 2-alkylpyrimidine from a 3-aminopropyl alkanecarboxylic acid amide which comprises passing the 3-aminopropyl alkanecarboxylic acid amide in the vapor phase over an acidic catalyst to produce a 2-alkyltetrahydropyrimidine; and subsequently passing the 2-alkyltetrahydropyrimidine in the vapor phase over a supported noble metal catalyst without the removal of water. This improvement eliminates the need to isolate the tetrahydropyrimidine and provides a method for the continuous conversion of the 3-aminopropyl amide to the pyrimidine in high yield.

In the preparation of 3-aminopropyl alkanecarboxylic acid amides from an alkanecarboxylic acid and 1,3-diaminopropane, two impurities are often encountered, unreacted carboxylic acid and a diamide in which each amino group of the diamine has reacted with some of the carboxylic acid. It has been found that these two impurities are significant poisons for the noble metal dehydrogenation catalysts of step c. Thus another aspect of the present invention is an improved process for the preparation of a 2-alkylpyrimidine from a 3-aminopropyl alkanecarboxylic acid amide which comprises reducing the level of any unreacted alkanecarboxylic acid and any N,N'-1,3-propanediylbis(alkanecarboxylic acid amide) in the feed stream prior to dehydrogenating said stream over a supported metal catalyst. This improvement significantly extends the lifetime of the dehydrogenation catalyst.

The most recent art recommends the preparation of the 3-aminopropyl alkanecarboxylic acid amide from the liquid phase, pressurized, batch reaction of a large excess of 1,3-diaminopropane and an alkanecarboxylic acid. The reaction must be conducted for extended periods of time under pressure. Another aspect of the present invention is an improved process for the preparation of a 2-alkyl-1,4,5,6- -tetrahydropyrimidine from 1,3-diaminopropane and an alkanecarboxylic acid which comprises contacting 1,3-diaminopropane and the alkanecarboxylic acid in the vapor phase over an acidic catalyst. The improved process increases yields and eliminates a pressurized batch reaction and the necessity to isolate the intermediate 3-aminopropyl alkanecarboxylic acid amide.

A further aspect of the present invention is an improved process for the preparation of a 2-alkylpyrimidine directly from 1,3-diaminopropane and an alkanecarboxylic acid in a dual catalyst system which comprises contacting 1,3-diaminopropane and the alkanecarboxylic acid in the vapor phase over an acidic catalyst and subsequently passing the resultant stream in the vapor phase over a supported noble metal catalyst. The water generated in the amidation and the cyclization/dehydration need not be removed.

BRIEF DESCRIPTION OF THE FIGURE

FIG. 1 schematically illustrates a continuous vapor phase process for the preparation of 2-tert-butylpyrimidine from 1,3-diaminopropane and pivalic acid.

DETAILED DESCRIPTION OF THE INVENTION

The present invention is directed to various process improvements in the conversion of 1,3-diaminopropane and an alkanecarboxylic acid to a 2-alkylpyrimidine. As used herein the terms "alkane" and "alkyl" refer to a straight-chained or branched hydrocarbon group of 1 to 4 carbon atoms inclusive. Branched alkyl groups of 3 to 4 carbon atoms are preferred. Iso-propyl and tert-butyl groups are most preferred. The conversion of 1,3-diaminopropane and an alkanecarboxylic acid to a 2-alkylpyrimidine involves the three chemical steps previously noted: amidation (step a): cyclization/dehydration (step b): and dehydrogenation (step c).

One aspect of the present invention is an improved process for the preparation of a 2-alkyl-1,4,5,6-tetrahydropyrimidine from a 3-aminopropyl alkanecarboxylic acid amide which comprises passing the 3-aminopropyl alkanecarboxylic acid amide over an acidic catalyst in the vapor phase. By an acidic catalyst is meant any solid material capable of forming a stable catalytic bed and having acidic sites which are capable of catalyzing the ring closure and dehydration of the 3-aminopropylamide to the tetrahydropyrimidine. Such materials include, for example, silica, alumina and zeolites.

The cyclization/dehydration reaction may typically be carried out like other vapor phase reactions in which the reactants and an appropriate diluent are mixed and passed over the catalyst at a contact time and temperature sufficient to achieve the desired conversion. Typically, an inert gas, such as, for example, nitrogen, is employed as a diluent. The mole ratio of diluent to starting material can be from about 1:1 to about 50:1. Approximately two to five moles of diluent per mole of 3-aminopropylamide are preferred. The reaction may be conducted with or without an additional solvent. Any polar or nonpolar organic solvent which dissolves the 3-aminopropylamide and which is stable to the dehydration and the subsequent dehydrogenation conditions is suitable for the process. Saturated aliphatic alcohols, such as, for example, methanol or aromatic hydrocarbons, such as toluene, are preferred if the use of a solvent is elected.

Although the exact residence time is not critical to prevent unnecessary degradation, the reactants should not be permitted to remain in contact with the catalyst for a prolonged period. The preferred contact period or residence time, which depends on several factors including the temperature within the operable ranges of temperature for a particular product, is readily determined by routine experimentation. Temperatures of from about 220° C. to about 300° C. provide reasonable reaction rates without appreciable formation of by-products. Temperatures of about 250° C. to about 275° C. are preferred.

Operating pressures are not critical and may vary from subatmospheric to somewhat superatmospheric. Atmospheric pressure is satisfactory and is preferred.

In a typical reaction, the 3-aminopropyl alkanecarboxylic acid amide, optionally in a solvent, and an inert diluent can be passed through a silica or alumina catalyst bed at about 250° C. to produce the 2-alkyl-1,4,5,6-tetrahydropyrimidine.

The tetrahydropyrimidine may be purified, for example, by distillation, or may, without further treatment or isolation, be dehydrogenated to give the 2-alkylpyrimidine.

This latter option provides a further aspect of the present invention, that is, an improved process for the preparation of a 2-alkylpyrimidine from a 3-aminopropyl alkanecarboxylic acid amide which comprises passing the 3-aminopropyl alkanecarboxylic acid amide over an acidic catalyst in the vapor phase and subsequently passing the resultant stream over a supported noble metal catalyst in the vapor phase without the removal of water.

Acidic catalysts have been previously defined. By a supported noble metal catalyst is meant any noble metal catalyst on a variety of supports that effects dehydrogenation. Such catalysts include but are not limited to platinum and palladium. Additionally, nickel and copper chromite may be used. Typical supports include silica alumina, magnesia and carbon. The preferred catalysts are platinum and palladium supported, for example, on alumina. The most preferred catalysts range from about 0.5 percent to about 1 percent palladium on alumina.

Similar to the cyclization/dehydration reaction, the dehydrogenation may typically be carried out like conventional vapor phase reactions. A gas, such as, for example, nitrogen or hydrogen is usually used as a diluent. About two to five moles of diluent per mole of 3-aminopropylamide are preferred. The cyclization-dehydrogenation reaction is best conducted without a solvent; however, various solvents that are inert towards the catalysts may be employed such as methanol or toluene.

For the initial stage, the cyclization/dehydration over the acidic catalyst can be conducted in the range of about 220° C. to about 300° C., preferably from about 250° C. to about 275° C. The dehydrogenation over the supported noble metal catalyst can be conducted in the range of about 280° C. to about 400° C., preferably from about 300° C. to about 340° C.

Again, operating pressures are not critical and atmospheric pressure is preferred.

In a typical reaction, neat 3-aminopropyl alkanecarboxylic acid amide along with a gaseous diluent is passed over a silica or alumina catalyst at approximately 250° C. and then a palladium on alumina catalyst at approximately 320° C. The twin catalyst system may be two interconnected but separate catalyst beds or a single bed in which the two catalysts are adjacent. The resulting 2-alkylpyrimidine may be isolated by condensation and purified by distillation.

Another aspect of the present invention is an improved process for extending the lifetime of a supported noble metal dehydrogenation catalyst for the preparation of a 2-alkylpyrimidine from a 3-aminopropyl alkanecarboxylic acid amide which comprises reducing the level of alkanecarboxylic acid and N,N'-1,3--propanediylbis(alkanecarboxylic acid amide) from the feed stream to be contacted with the dehydrogenation catalyst. A supported noble metal catalyst has been previously defined.

The reduction in the levels of alkanecarboxylic acid and N,N'-1,3-propanediylbis(alkanecarboxylic acid amide) in the feed going to the dehydrogenation catalyst can be accomplished by either physical or chemical means. In addition, the reduction can occur at either the 3-aminopropyl alkanecarboxylic acid amide or the 2-alkyltetrahydropyrimidine stage.

By way of example, crude 3-aminopropyl pivalamide can be purified by recrystallization from either aromatic hydrocarbons such as toluene or from chlorinated hydrocarbons such as perchloroethylene. Levels of pivalic acid of up to 3 percent and of N,N'- -1,3-propanediyl-bis(pivalamide) of up to 9 percent can be reduced to less than 0.1 percent by recrystallization. Alternatively, crude 3-aminopropyl pivalamide can be chemically treated with base to neutralize any pivalic acid and the 3-aminopropyl pivalamide can be separated from the salt of pivalic acid and the bis(pivalamide) by vacuum distillation.

In a similar vein, reduction in the levels of pivalic acid and the bis(pivalamide) can also be accomplished at the tetrahydropyrimidine stage. For example, the level of bis(pivalamide) can be conveniently reduced from 2-tert-butyl-1,4,5,6- -tetrahydropyrimidine produced in the previously described continuous twin-catalyst process by the controlled condensation of the bis(pivalamide) prior to introduction to the dehydrogenation catalyst bed.

By reducing the level of alkanecarboxylic acid and of N,N'-1,3-propanediylbis(alkanecarboxylic acid amide), the effective lifetime of the supported noble metal dehydrogenation catalyst can be greatly extended. •

Another aspect of the present invention is an improved process for the preparation of a 2-alkyl- -1,4,5,6-tetrahydropyrimidine directly from 1,3- -diaminopropane and an alkanecarboxylic acid which comprises contacting 1,3-diaminopropane and the alkanecarboxylic acid in the vapor phase over an acidic catalyst. The term acidic catalyst has previously been defined as any solid material capable of forming a catalytic bed and having acidic sites which are capable of catalyzing the ring closure and dehydration of a 3-aminopropylamide to a tetrahydropyrimidine. In the present context, the acidic catalyst is further defined as also being capable of catalyzing the amidation reaction between an alkanecarboxylic acid and 1,3-diaminopropane to form the 3-aminopropylamide. The preferred catalysts remain silica and alumina.

The sequential amidation and cyclization/dehydration reactions may typically be carried out like other vapor phase reactions in which the reactants and an appropriate diluent are mixed and passed over the catalyst at a contact time and temperature sufficient to achieve the desired conversion. Typically, an inert gas, such as, for example, nitrogen, is employed as a diluent. The mole ratio of diluent to starting material can be from about 1:1 to about 50:1. Approximately 2 to 5 moles of diluent per mole of reactants are preferred. The reaction may be conducted with or without an additional solvent. Any solvent capable of dissolving the salt of the alkanecarboxylic acid and 1,3-diaminopropane is suitable for the process. Water or methanol are preferred if the use of a solvent is elected.

The use of an excess of 1,3-diaminopropane relative to alkanecarboxylic acid increases the selectivity for tetrahydropyrimidine formation. Thus although a stoichiometric ratio of 1,3-diaminopropane to alkanecarboxylic acid may be employed, molar ratios of about 1.1:1 to about 6:1 of diamine to acid are preferred.

Although the exact residence time is not critical to prevent unnecessary degradation, the reactants should not be permitted to remain in contact with the catalyst for a prolonged period. The preferred contact period or residence time, which depends on several factors including the temperature within the operable ranges of temperature for a particular product, is readily determined by routine experimentation. Temperatures of from about 220° C. to about 300° C. provide reasonable reaction rates without appreciable formation of by-products. Temperatures of about 250° C. to about 275° C. are preferred.

Operating pressures are not critical and may vary from subatmospheric to somewhat superatmospheric. Atmospheric pressure is satisfactory and is preferred.

In a typical reaction, the alkanecarboxylic acid and 1,3-diaminopropane are mixed together in the desired ratio and in a solvent if desired. The mixture is passed over a silica or alumina catalyst bed at about 250° C with an inert diluent at atmospheric pressure. The tetrahydropyrimidine produced can be isolated by removal of excess 1,3-diaminopropane/water by distillation under vacuum or may, without isolation, be dehydrogenated to a 2-alkylpyrimidine.

Again this latter option provides a further aspect of the present invention, that is, an improved process for the preparation of a 2-alkylpyrimidine directly from 1,3-diaminopropane and an alkanecarboxylic acid in a dual catalyst system which comprises contacting 1,3-diaminopropane and the alkanecarboxylic acid in the vapor phase over an acidic catalyst and subsequently passing the resultant stream in the vapor phase over a supported noble metal catalyst. The term acidic catalyst refers to a material that is catalytic for both the amidation and the cyclization/dehydration reactions as defined above. The preferred acidic catalysts are silica and alumina. The term supported noble metal catalyst refers to a noble metal dehydrogenation catalyst supported on a typical support material as defined above. The preferred dehydrogenation catalysts are platinum and palladium supported, for example, on alumina.

The sequential amidation, cyclization/dehydration and dehydrogenation reactions may typically be carried out like other vapor phase reactions in which the reactants and an appropriate diluent are mixed and passed over the catalyst at a contact time and temperature sufficient to achieve the desired conversion. Typically, a gaseous diluent, such as, for example, nitrogen or hydrogen, is employed. Hydrogen is the most preferred diluent in terms of extending the lifetime of the dehydrogenation catalyst. The mole ratio of diluent to starting material can be from about 1:1 to about 50:1. Approximately 2 to 5 moles of diluent per mole of reactant are preferred. The reaction is best conducted without a solvent, but solvents capable of dissolving the salt of the alkanecarboxylic acid and 1,3-diaminopropane, such as water or methanol, may be optionally employed.

The alkanecarboxylic acid and 1,3-diaminopropane are preferably used in equal molar amounts, although a moderate excess of diamine (approximately 2:1) may be used to ensure adequate conversion of the carboxylic acid. Although operable, larger excesses of either reagent are impractical and would entail costly recovery steps and contribute to the deactivation of the dehydrogenation catalyst.

Although the exact residence time is not critical to prevent unnecessary degradation, the reactants should not be permitted to remain in contact with the catalyst for a prolonged period. The preferred contact period or residence time, which depends on several factors including the temperature within the operable ranges of temperature for a particular product, is readily determined by routine experimentation. For the initial stage, the amidation and the cyclization/- dehydration over the acidic catalyst can be conducted in the range of about 220° C. to about 300° C., preferably from about 250° C. to about 275° C. The subsequent dehydrogenation over the supported noble metal catalyst can be conducted in the range from about 280° C. to about 400° C., preferably from about 300° C. to about 340° C.

Operating pressures are not critical and may vary from subatmospheric to somewhat superatmospheric. Atmospheric pressure is satisfactory and is preferred.

The reduction in the levels of alkanecarboxylic acid and N,N'-1,3-propanediylbis(alkanecarboxylic acid amide) from the feed prior to introduction to the dehydrogenation catalyst bed promotes extended catalyst lifetimes and is preferred. The twin catalyst system may be two interconnected but separate catalyst beds or a single bed in which the two catalysts are adjacent. Separate catalyst beds with a means for reducing the level of carboxylic acid and diamide located between their interconnection are preferred.

A vapor phase reaction system for the continuous production of 2-tert-butylpyrimidine from 1,3-diaminopropane and pivalic acid is illustrated in FIG. 1. In a typical reaction, pivalic acid and 1,3-diaminopropane in approximately equal molar amounts, either in an aqueous solution or separately using no solvent, are passed in the presence of hydrogen over an alumina bed at 275° C. at atmospheric pressure. The resulting vapors are passed through a connecting line and trap held from about 250° C. to about 280° C. to condense higher-boiling impurities and over a second bed of palladium on alumina catalyst at 320° C. The vapors can be condensed and purified by distillation.

The present invention is illustrated by the following examples; however, the examples should not be interpreted as a limitation upon the scope of the present invention.

EXAMPLE 1 a) Preparation of 2-tert-butyl-1,4,5,6tetrahydropyrimidine (THP) from N-(3-aminopropyl)-2,2-dimethylpropanamide (APPA)

A 26 percent by weight solution of APPA (204 gs) in methanol was pumped at a rate of 29 grams (g) of APPA per hr (hr) over a 79g bed of activated silica gel (6–12 mesh) held at 250° C. The bed size was approximately 25 inches (") in length with a ½" diameter. A slow nitrogen purge of 40 mL/minute (min) was maintained through the bed during the run. The vapors were condensed and collected at the bottom of the bed, accounting for 97.6 percent mass recovery of the material pumped into the bed. Analysis by gas chromatography (GC) indicated that this solution contained 21 percent by weight THP, with nearly 100 percent conversion of APPA. The obtained weight represented an 84 percent yield of THP based on the weight of APPA pumped to the bed.

b) Preparation of 2-tert-butylpyrimidine (TBP) from 2-tert-butyl-1,4,5,6-tetrahydropyrimidine (THP)

Without further treatment, the methanol/THP solution was pumped at a rate of 42 g of THP per hr over a 96 g catalyst bed consisting of 1 percent palladium on ⅛" alumina pellets, held at 270° C. The bed size was approximately 25" in length with a ½" diameter. A slow nitrogen purge of 40 mL/min was maintained through the bed during the run. The vapors were condensed and collected at the bottom of the bed, accounting for 89.3 percent mass recovery of the material pumped into the bed. Analysis by GC indicated that this solution contained 22 percent by weight of TBP, with nearly 100 percent conversion of THP. The obtained weight represented an 89 percent yield of TBP based on THP, or a 75 percent yield of TBP based on the amount of APPA used above.

EXAMPLE 2

Preparation of 2-tert-butylpyrimidine (TBP) from N-(3-aminopropyl)-2,2-dimethylpropanamide (APPA)

APPA of sufficient purity for the cyclization/dehydrogenation reaction was prepared by contacting pivalic acid with a three-fold excess of 1,3-diaminopropane at 220° C. for 13 hours (hrs) in a pressure vessel. This was followed by first a vacuum strip of excess 1,3-diaminopropane, and then a high- -vacuum flash distillation of APPA to separate it from the high-boiling diamide. Analysis of the APPA overheads by GC indicate a purity of greater than 95 percent. The levels of pivalic acid and diamide were found to be 0.4 percent and 1.1 percent weight percent respectively.

Molten APPA (1169 g) held at 80-100° C. on a hot plate stirrer was pumped at a rate of 26 g per hr through a 150° C. preheated line over a catalyst system comprised of 25 g of ⅛" silica pellets held at 250° C., and 37 g of 1 percent palladium on ⅛" alumina pellets held at 320° C. The silica bed size was 18"×½" and the palladium bed size was 9"×½". A nitrogen purge of 90 mL/min was maintained through the system. The vapors were condensed and collected at the bottom of the bed, accounting for 92.0 percent mass recovery of the material pumped into the bed. The liquid product was monitored periodically throughout the run by GC in order to monitor the activity of the catalyst. Table I of conversion versus time is shown below.

TABLE I

| Time (Hours) | Percent Conversion to TBP |
| --- | --- |
| 5 | 100 |
| 10 | 100 |
| 20 | 99 |
| 25 | 97 |
| 30 | 95 |
| 40 | 95 |
| 45 | 94 |

Analysis of the final product by GC indicated that this solution was 76 weight percent TBP, representing an 82 percent yield based on the weight of APPA pumped into the reactor.

EXAMPLE 3 a) Purification of N-(3-aminopropyl)-2,2-dimethylpropanamide (APPA): removal of pivalic acid and N,N'-1,3-propanediylbis (2,2-dimethylpropanamide) (diamide)

Crude APPA (3312 g), consisting of 84 percent APPA, 2 percent THP, 9 percent diamide, and 2 percent pivalic acid, was warmed to a molten state (80° C.) and dissolved in 7400 g toluene in a 20 liter jacketed flask attached to a Dowtherm ® heating/cooling system. The stirred solution was cooled to 15° C. and seeded. Crystal formation was indicated by a temperature rise to 21° C. The stirred slurry was drained and the fine crystals collected on a glass funnel and suction dried in air for ca. 30 min. The solid was placed under high vacuum for a few hrs to remove most of the toluene solvent, then stirred in the molten state at 75° C. under high vacuum for two hrs to remove traces of toluene. The weight of APPA thus obtained was 1608 g, and analysis by GC showed a purity of 99 percent APPA 0.1 percent diamide, less than 0.1 percent pivalic acid, and 1 percent THP by weight.

b) Preparation of 2-tert-butylpyrimidine (TBP) from N-(3-aminopropyl)-2,2-dimethylpropanamide (APPA).

Purified APPA obtained in this manner was used in the cyclization/dehydrogenation reaction. Molten APPA (3152 g) held at 80-100° C. on a hot plate stirrer was pumped at a rate of 28.7 g per hr through a 150° C. preheated line over a catalyst system comprised of 26.6 gs of ⅛" silica pellets held at 250° C. and 36.9 g of 1 percent palladium on ⅛" alumina pellets held at 320° C. The silica bed size was 18"×½" and the palladium bed size was 9"×½". A nitrogen purge of 90 mL/min was maintained through the system. The vapors were condensed and collected at the bottom of the bed, accounting for 92.4 percent mass recovery of the material pumped into the bed. The liquid product was monitored periodically throughout the run by GC in order to monitor the activity of the catalyst. After 54 hrs, the palladium bed temperature was periodically increased in 10° increments in order to maintain a high level of conversion of THP to TBP as the catalyst gradually deactivated. Table II summarizing conversion versus time is shown below.

TABLE II

| Time (Hours) | Pd Bed (°C.) | Percent Conversion to TBP |
| --- | --- | --- |
| 1 | 320 | 100 |
| 7 | 320 | 100 |
| 26 | 320 | 98 |
| 35 | 320 | 97 |
| 40 | 320 | 97 |
| 45 | 320 | 97 |
| 50 | 320 | 97 |
| 55 | 330 | 98 |
| 56 | 340 | 99 |
| 60 | 340 | 98 |
| 70 | 340 | 97 |
| 80 | 350 | 97 |
| 90 | 350 | 97 |
| 97 | 360 | 98 |
| 100 | 360 | 97 |
| 104 | 370 | 98 |
| 110 | 370 | 97 |

The weight of the crude TBP obtained after 110 hrs. was 2838 g, and analysis of this solution by GC indicated that it was 83 percent by weight TBP, representing an 86 percent yield of TBP based on the weight of APPA pumped into the reactor.

c) Regeneration of dehydrogenation catalyst bed

The catalyst bed was regenerated by first washing the cooled bed at room temperature with isopropanol and methanol, heating to 300° C. (the silica bed was heated only to 250° C.), and passing an air/steam/nitrogen mixture through the bed at a rate of 300 mL/min, 0.7 mL/min (as water through the feed line), and 1200 mL/min, respectively for 1 hr. An exotherm of 71° was observed on the palladium bed. No exotherm was observed on the silica bed. The bed, after purging with pure nitrogen for ten mins, was finally treated with a nitrogen/hydrogen mixture at a rate of 565 mL/min and 340 mL/min respectively for 45 mins. The hydrogen flow was terminated and the bed purged with pure nitrogen.

The cyclization/dehydrogenation reaction was resumed as above for an additional 49 hrs using recrystallized APPA feed. Although the initial catalyst activity has been restored, the rate of deactivation is somewhat faster than that of a fresh catalyst. Table III indicating conversion versus time is shown below.

TABLE III

| Time (Hours) | Pd Bed (°C.) | Percent Conversion to TBP |
|---|---|---|
| 1 | 320 | 100 |
| 5 | 320 | 99 |
| 10 | 320 | 98 |
| 20 | 320 | 97 |
| 24 | 330 | 98 |
| 30 | 330 | 97 |
| 32 | 340 | 98 |
| 39 | 340 | 96 |
| 41 | 350 | 98 |
| 44 | 350 | 97 |
| 46 | 360 | 98 |
| 49 | 360 | 97 |

An additional 1253 g of crude TBP was obtained in this run with the regenerated catalyst. Analysis of the product by GC shows a TBP purity of 85 percent, representing an 87 percent yield of TBP based on the weight of APPA pumped into the reactor.

The two runs produced a total of 3412 g of TBP from 4559 g of APPA feed, representing a total catalyst lifetime of 92 g of TBP per gram of catalyst.

EXAMPLE 4

Preparation of
2-tert-butyl-1,4,5,6-tetrahydropyrimidine (THP) from pivalic acid and 1,3-diaminopropane a) 1/6 Reactant Ratio

A mixture of pivalic acid (25 g, 0.24 mole) and 1,3-diaminopropane (106 g, 1.43 mole) was pumped at a rate of 0.5 g/min into a 65.2 g bed of Alcoa alumina CSS-300 $\frac{1}{8}$" Low Density Spheres heated to 250° C. The bed size was $\frac{1}{2}$" diameter by 27" length. A nitrogen purge of 100 mL/min was maintained through the system. The vapors were condensed and collected at the bottom of the bed, and a sample was analyzed by GC. Solid 2-t-butyltetrahydropyrimidine (THP) was crystallized from the liquid product. A total of 110.7 g of product was condensed from the reactor, representing an 85 percent mass recovery. Table IV below shows the product composition from this run.

b) $\frac{1}{3}$ Reactant Ratio

A mixture of pivalic acid (21 g, 0.21 mole) and 1,3-diaminopropane (46 g, 0.62 mole) was pumped at a rate of 0.5 g/min into an alumina bed as in Example 4a above, and a total of 56.5 g of product was condensed from the reactor, representing an 84 percent mass recovery. Table IV below shows the product composition from a sample of this run.

c) 1/1.2 Reactant Ratio in Water

A solution of pivalic acid (71 g, 0.69 mole), 1,3-diaminopropane (62 g, 0.83 mole), and water (120 g, 6.6 mole) was pumped at a rate of 0.5 g/min into an alumina bed as in Example 4a above, and a total of 198 g of liquid product was condensed from the reactor, representing a mass recovery of 84 percent. Table IV below shows the product composition from a sample of this run.

TABLE IV

| (Product Composition of 4a)(–c) Weight Percent | | | |
|---|---|---|---|
| Pivalic Acid | Diamide | APPA | THP |
| (a) 0 | 0 | 4 | 27 |
| (b) 0.2 | 0.5 | 8 | 18 |
| (c) 1.5 | 3.5 | 29 | 8 |

EXAMPLE 5

Preparation of 2-tert-butylpyrimidine (TBP) from pivalic acid and 1,3-diaminopropane The alumina catalyst was Alcoa CSS-300, LDS $\frac{1}{8}$" macroporous spheres. The palladium catalyst was Engelhard 1 percent Pd on $\frac{1}{8}$" alumina pellets. The alumina bed contained 68 g of catalyst and was $\frac{1}{2}$" diameter by 28$\frac{1}{2}$" in length. The second bed contained a 20 g portion of alumina ($\frac{1}{2}$"×8$\frac{1}{2}$" length), followed by 36 g of Pd catalyst ($\frac{1}{2}$"×9$\frac{1}{2}$" length). A heated line (250° C.) connected the two beds, and contained a trap system held at 280° C. which served to hold any high-boiling diamide and prevent its passage over the Pd catalyst. A 100 mL/min hydrogen stream was passed through the reactor during the run.

Pivalic acid (160 g, 1.57 mole), 1,3-diaminopropane (150 g, 2.02 mole), and water (114 g, 6.33 mole) were carefully mixed together, and pumped at a rate of 35.3 g/hr into a 275° C. preheater zone then through the alumina bed held at 275° C., and then through the palladium bed held at 320° C. The vapors were passed down the first bed, through the connecting line and trap, then up the second bed and condensed at the top and collected as a liquid. A total of 350.6 g of product was obtained, representing an 83 percent mass recovery. The product was obtained as two phases, an organic and aqueous phase. Capillary GC analysis showed the organic phase to consist of 82 percent by weight TBP, and the aqueous phase to consist of 4.7 percent by weight TBP. This represents a 72 percent total yield of TBP based on pivalic acid, and a 55 percent yield based on 1,3-diaminopropane.

The reaction may also be carried out as above, but without the use of water solvent by pumping pivalic acid and 1,3-diaminopropane through separate lines directly into the preheater zone.

What is claimed is:

1. A process for preparing a 2-($C_1$–$C_4$) alkylpyrimidine directly from 1,3--diaminopropane and a ($C_1$–$C_4$) alkanecarboxylic acid which comprises the steps of:
   (a) contacting in the vapor phase from about one to about two molar equivalents of 1,3- -diaminopropane with about one molar equivalent of ($C_1$–$C_4$)alkanecarboxylic acid in the presence of a hydrogen diluent at a temperature from about 220° C. to about 300° C. over an alumina or silica catalyst;
   (b) reducing the level of N,N'-1,3- -propanediylbis-(($C_1$–$C_4$)alkanecarboxylic acid amide); and
   (c) passing the resultant stream in the vapor phase at a temperature from about 280° C. to about 400° C. over a supported platinum or palladium catalyst.

2. The process of claim 1 wherein the 2-($C_1$–$C_4$)alkylpyrimidine is 2-tert-butylpyrimidine, the ($C_1$–$C_4$)alkanecarboxylic acid is pivalic acid and the N,N'-1,3- propanediylbis-(($C_1$–$C_4$)alkanecarboxylic acid amide) is

N,N'-1,3-propanediylbis(pivalamide).

3. The process of claim 2 wherein step (a) is conducted from about 250° to about 275° C. and step (c) is conducted from about 300° to about 340° C.

4. The process of claim 3 wherein the level of the N,N'-1,3-propanediylbis(pivalamide) is reduced by selective condensation.

* * * * *